(12) United States Patent
Ben David

(10) Patent No.: US 7,662,342 B2
(45) Date of Patent: Feb. 16, 2010

(54) MEASURING CELL

(75) Inventor: Tsur Ben David, Ramat Hasharon (IL)

(73) Assignee: Blue I Water Technologies Ltd., Kfar Saba (IL)

( * ) Notice: Subject to any disclaimer, the term of this patent is extended or adjusted under 35 U.S.C. 154(b) by 597 days.

(21) Appl. No.: 10/596,308

(22) PCT Filed: Dec. 8, 2003

(86) PCT No.: PCT/IL03/01038

§ 371 (c)(1),
(2), (4) Date: Jun. 8, 2006

(87) PCT Pub. No.: WO2005/054824

PCT Pub. Date: Jun. 16, 2005

(65) Prior Publication Data

US 2007/0092406 A1    Apr. 26, 2007

(51) Int. Cl.
*G01N 21/00* (2006.01)
(52) U.S. Cl. .................. 422/82.05; 422/99; 422/100; 204/193; 15/1.7; 15/104.03; 436/180
(58) Field of Classification Search ............. 204/195, 204/193; 422/99–100, 82.05; 15/1.7, 104.061, 15/104.03; 436/180
See application file for complete search history.

(56) References Cited

U.S. PATENT DOCUMENTS

| 2,974,338 | A | * | 3/1961 | Florenz et al. ............... 15/160 |
| 3,402,116 | A | * | 9/1968 | Kaltenhauser et al. ...... 204/402 |
| 3,956,094 | A |   | 5/1976 | Capuano |
| 5,185,531 | A |   | 2/1993 | Wynn |
| 5,824,270 | A |   | 10/1998 | Rao |
| 6,180,412 | B1 |  | 1/2001 | Kroll |
| 2002/0130069 | A1 | | 9/2002 | Moskoff |

FOREIGN PATENT DOCUMENTS

WO    00/02031    1/2000

* cited by examiner

*Primary Examiner*—Jill Warden
*Assistant Examiner*—Jyoti Nagpaul
(74) *Attorney, Agent, or Firm*—Lowe Hauptman Ham & Berner, LLP

(57) ABSTRACT

The invention relates to a spectrophotometric measuring cell, useful for automated reagent mixing and for handsfree physical cleansing comprising: a measuring cell; a shaker; and an actuator. The invention also relates to a method for automatically mixing of fluids and/or reagents and for handsfree physical cleansing of the inner core of spectrophotometric measuring cells.

13 Claims, 2 Drawing Sheets

MEASURING CELL

FIELD OF THE INVENTION

The present invention generally relates to a measuring cell. In particular to measuring cells for swimming pools systems.

BACKGROUND OF THE INVENTION

Chlorine is often added to drinking water supplies to kill harmful microorganisms. Chlorine is not only an effective disinfectant, but it also reacts with ammonia, iron and other metals and some organic compounds to improve overall water quality. There is a limit to the use of chlorine, however, as negative results are possible with the addition of too much chlorine. Bad tastes or odors in water are often enhanced. Excess chlorine can be harmful to fish and other aquatic animals when the water contains nitrogen compounds. Finally, the formation of chloroform and other suspected carcinogens is possible. It is thus very important for water suppliers to monitor closely the levels of chlorine present in the water for which they are responsible. Practically, water systems look for a level of chlorine remaining in the water after treatment to be 1 mg/L or less for minimizing adverse effects while maintaining disinfectant properties. Above 1 mg/L, odor and taste often become problematic.

A method and apparatus for the measurement of amounts of free available chlorine in solution have been described in U.S. Pat. No. 3,956,094 and other patents. The apparatus includes a sensing electrode, which is internally, and a reference electrode supported within a container. The electrode surface is continuously washed by the pH control solution. The method and apparatus of the present invention is adapted to be used, for example, to measure the free available chlorine concentration in swimming pool waters. Nevertheless, the dependency on said fragile and ever blockaged sensing electrode, as well as the requirement for a routine cleansing operation, which usually requires manually routine of disintegrating the assembly accommodating the electrode, cleansing operation and vis versa eliminates the use of said method.

Yet another and more efficient method was presented, see for example U.S. Pat. No. 6,180,412 to determine photometrically chlorine concentration in water. The method of determining chlorine in this experiment relies on a color indicator, usually N,N-diethyl-p-phenylene-diamine, denoted in its short and known term 'DPD'. In the presence of chlorine, DPD reacts rapidly to form a red color, the intensity of which is an indicator of chlorine concentration. The higher the absorbance, the higher the chlorine concentration. Thought the photochemical reaction is pH sensitive, DPD/chlorine system typically appears in a red color, measured at about 515 nm. At a near neutral pH, the primary oxidation product is a semi-quinoid cationic compound known as a Wurster dye. The DPD Wurster dye color has been measured photo-metrically at wavelengths ranging from 490 to 555 nm.

A measuring cell useful for a routine determination of fluids, having mechanical means to clean the inner core of the measurement cell was not presented in art. It is thus the aim of the present invention to provide a novel spectrophotometric measuring cell, useful for automated reagent mixing and for handsfree physical cleansing.

BRIEF DESCRIPTION OF THE FIGURES

In order to understand the invention and to see how it may be carried out in practice, a preferred embodiment will now be described, by way of non-limiting example only, with reference to the accompanying drawing, in which.

SUMMARY OF THE INVENTION

Figure 1:
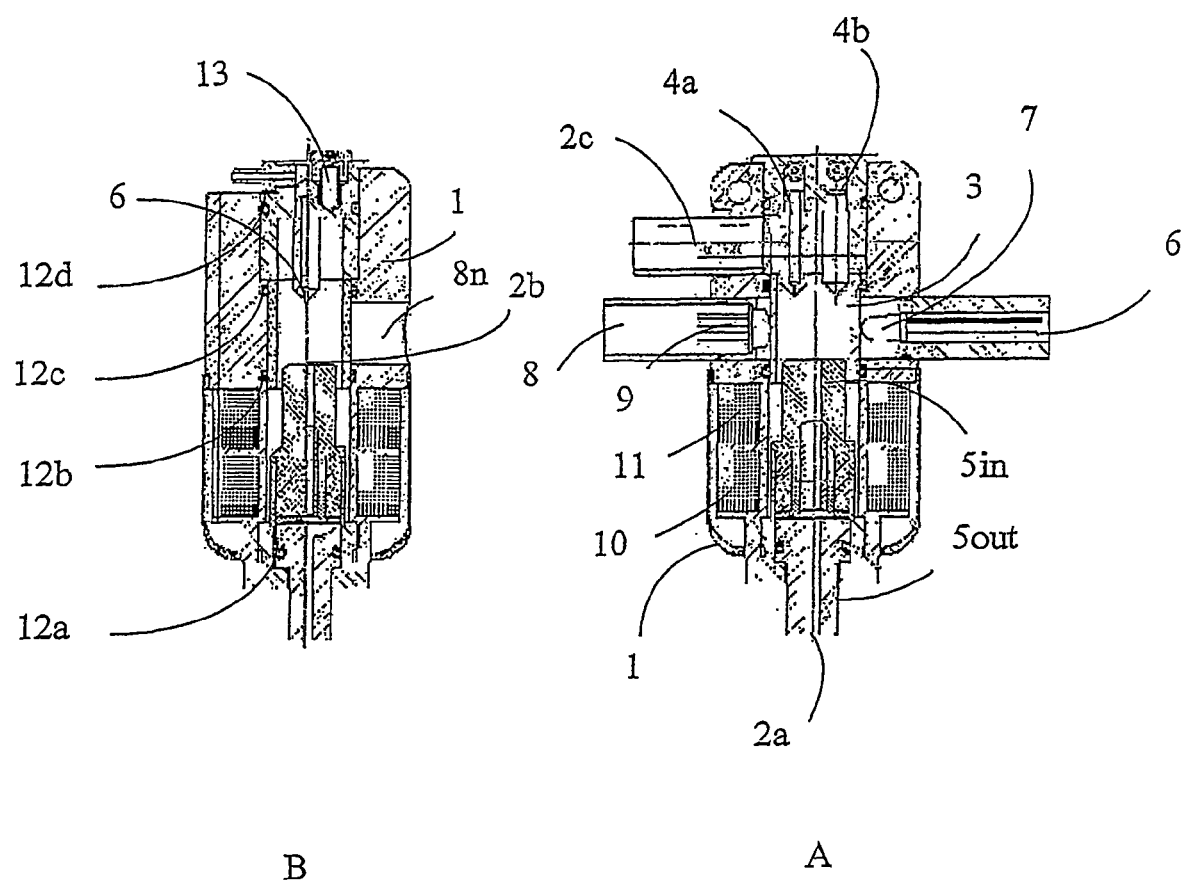
FIG. 1A and FIG. 1B present a cross section of the measuring cell according to one embodiment of the present invention.

It is the scope of the present invention to present a spectrophotometric measuring cell, useful for automated reagent mixing and for handsfree physical cleansing. Said measuring cell comprising a measuring cell having a free fluid passageway throughout its inner bore from an inlet to an outlet, comprising a light-transparent measuring tube characterize by a longitudinal axis a, and a inner bore of a diameter b; a shaker, accommodated in said tube'd inner bore; having means to strike back and forth along the axis a, comprising a brush of an outer diameter b, said brush is adapted to provide an effective physical cleansing of the inner wall of the cell at the time the shaker is moving along its course; and an actuator, located outside the said tube, adapted to reversibly actuate said shaker to a predetermined rate and course. Fluids and/or reagents filling the measuring tube are effectively mixed by means of at least one of the shaker's strikes to obtain a homogenized solution and wherein a necessity of manually cleansing routine is thus avoided.

The measuring cell is especially useful for water systems, selected from swimming pools, water treatment facilities, sewage treatment plants, drinking water systems, cooling towers, or any on-line measurement of water. This measuring cell is most particularly useful for swimming pools and related water systems, having means to measure parameters selected from pH, Redox, free chlorine content, light scattering, turbidity and temperature.

It is also in the scope of the present invention to present a method for automatically measuring predetermined parameters of the fluids.

DETAILED DESCRIPTION OF THE INVENTION

The following description is provided, along all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide the measuring cell defined below.

It is thus a primary goal of the present invention to present a novel spectrophotometric measuring cell, useful for automated reagent mixing and for handsfree physical cleansing. The said measuring cell comprises of at least three components as follows: a measuring cell, a shaker and an actuator. The measuring cell is characterized by that whereat fluids and/or reagents are filling the measuring tube, they are effectively mixed by means of at least one of the shaker's strikes to obtain a homogenized solution. In this way, a tedious necessity of manually cleansing routine is thus avoided.

The measuring cell is having a free fluid passageway throughout its inner bore from an inlet to an outlet. The cell is made of any metal or polymer, and comprising a light-transparent measuring tube characterized by a longitudinal axis a, and a inner bore of a diameter b. In addition, the spectrophotometric measuring cell comprising a detector, which is having means to measure either monochromatic wavelength or a multi-channeled RGB light emission of a broad spectra range. The measuring tube is preferably made of a light transparent glass, quartz or polymer.

The shaker is accommodated in said tube's inner bore and having means to strike back and forth along the axis a. Said shaker comprising a brush of an outer diameter b. The brush is adapted to provide an effective physical cleansing of the inner wall of the cell at the time the shaker is moving along its course. The shaker is preferably made in at least in its portion of stainless steel. The brush is preferably made of nylon fibers. A helix-like pattern of said fibers is preferred, because said pattern provides for a screw-like movement of the shaker inside the measuring tube and so to a better cleansing mechanism. Said shaker is also referring in the present invention to the terms self-cleaning assembly (i.e., ASC™), and to active reagent mixer (i.e., ARM™).

The actuator is located outside the said measuring tube, and is adapted to reversibly actuate said shaker to a predetermined rate and course. According to one embodiment of the present invention, the aforementioned actuator is comprises of at least one electromagnetic coil, adapted to actuate the shaker magnetically. According to another embodiment of the present invention, the said actuator comprising at least two electromagnetic actuators: at least one adapted to move the shaker upwards, and at least one adapted to move the shaker downwards.

Moreover, the present invention relates to a measuring cell useful to determine predetermined biological, physical and/or chemical parameters. The fluids to be sampled and determined are thus selected from any industrial, urban, domestic, medical, fluids driven from the body of a patient or any other fluids, liquids, solvents, gassed solutions and any mixture of the same. All said fluids defined above are referring in the present invention to the term 'fluid'.

The measuring cell defined above is useful for water systems, selected from swimming pools, water treatment facilities, sewage treatment plants, drinking water systems, cooling towers, or any on-line measurement of water.

It is still well in the scope of the present invention, wherein the hereto-defined measuring cell is especially and particularly useful for monitoring and maintaining water in swimming pools. In this embodiment of the present invention, the measuring as defined in any of the above, having means to measure parameters selected from pH, Redox, free chlorine content, light scattering, turbidity and temperature. Hydro-Guard™ HG-302 is one commercially available apparatus comprising from now the characteristics defined in the present invention, namely the self-cleaning assembly (i.e., ASC™), and the active reagent mixer (i.e., ARM™).

Figure 2:
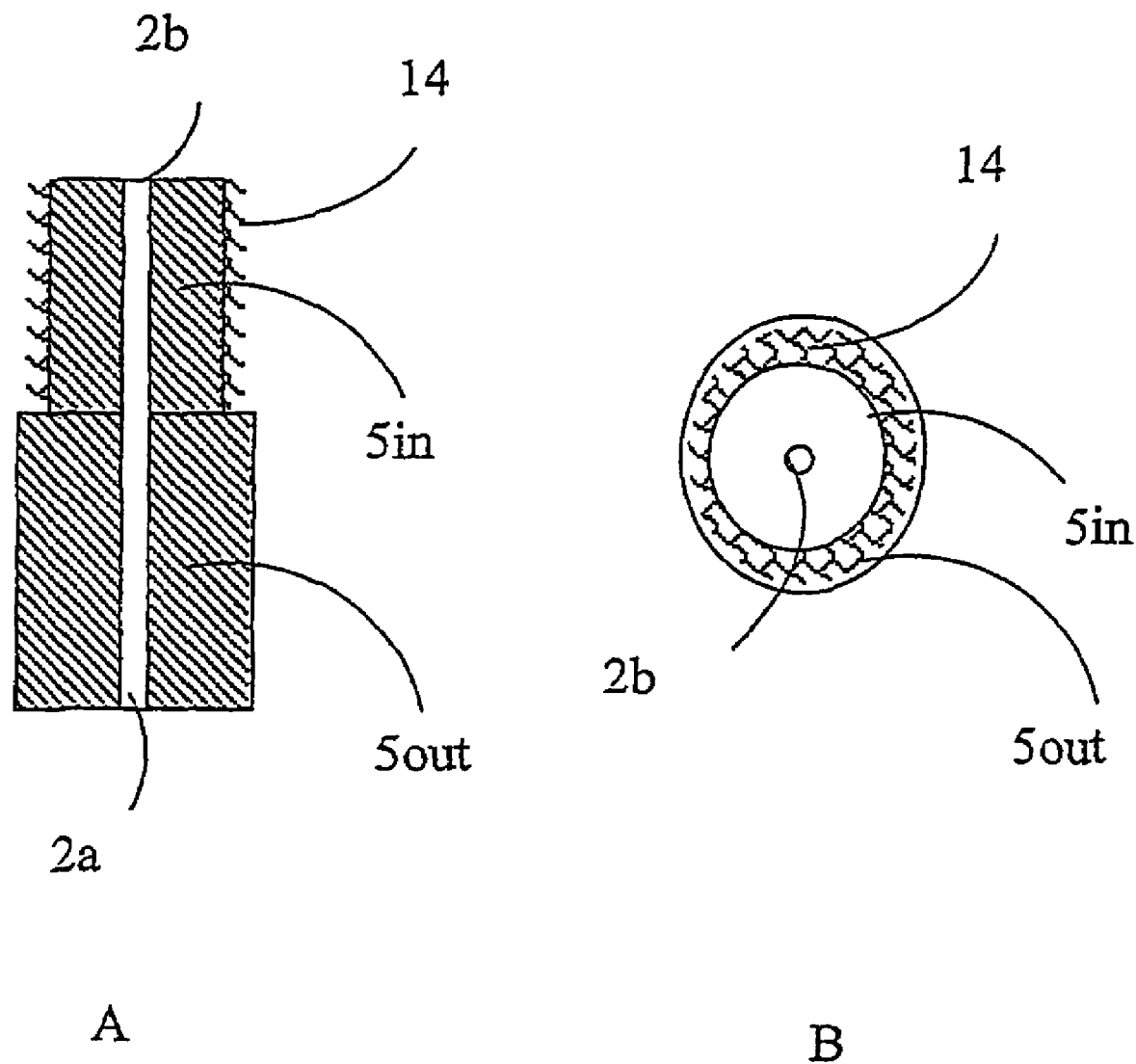
FIG. 2A and FIG. 2B present a cross section of one type of a shaker (2A) and a top view of the same.

Reference is made now to FIG. 1A, presenting a schematic cross section of the measuring cell (1) as defined in some of the above embodiments. FIG. 1B shows the very same measuring cell (1) placed in a rotation of 90°. FIGS. 2A and 2B will thus simultaneously provided for defining the same embodiment. Fluid inlet (2a) is located in the lower rim of the shaker (5), so fluid to be sampled is inflow to the inner volume of measuring tube (3), and after the measurement was proceeded, the fluid is outflow via outlet (2c), photochemical reactions are provided in the inner bore of the tube (3), whereat at least one reagent's inlet orifices are open. The embodiment presented in FIG. 1 especially useful for the determination of free chlorine in pools and running waters. Thus, orifice (4a) is adapted for DPD inlet, and orifice (4b) is designed for a buffer supply.

It is acknowledged in this respect that supply of DPD and duffer in a liquid state is a unique to the present invention, wherein utilization of the DPD in its solid form, such as in tablets or powders are known in the art. Thus, coupling DPD addition with its proper diluent provides for the user to determine the color characteristics of the reaction. According to one preferred embodiment of the present invention, the DPD Wurster dye color has been measured to yield with a color of about 490 to 555 nm.

After the reagents are injected from their inlet orifices (4a, 4b), the shaker (5) defined above is striking a plurality of strikes, effectively about three subsequent strikes. Each of those strikes can be characterized according to one embodiment of the invention as a gradually and sudden movement of the shaker upwards, downwards and vis versa. Said strikes are provided by means of the actuator. According to the present embodiment, two electromagnetic coils arrange in a line are providing the upward movement (actuator 10) and the downward movement (actuator 11). Thus, according to this embodiment, at least a portion of the shaker is made of magnetic metals, which are coated with suitable rubber or polymer.

The said plurality of strikes of the shaker provides for at least four advantages, selected from the flowing group: (a) mixing the reagents with the sampled fluid; (b), mechanically cleansing the inner bore of the measuring tube; (c) purging excess of gases or air bubbles via outlet (13) to a liquid/gas separator (not shown); and (d) provides for an accurate zero reading when the strike proceeds before reagent injection.

The photochemical reaction may be illuminated with either a monochromatic light source (such a filtered LED, LASER etc), or by a plurality of light sources or a polychromatic one light source. Reference is made thus to opening (6) adapted to accommodate a suitable LED (7).

Opening (8) located in a 180 axis referring the opening (6) is adapted to accommodate the light sensor (9). According to a novel characteristic of the present invention, a plurality of standardized RGB color sections may simultaneously detected, and animated-displayed at real time. For example a Mazet made MCS-EB1 components may be used. This is a programmable CVC having the following characteristics: 10-Bit ADC, µC 8052 RS232 interface, 4× achromatic light LED, Operating Voltage 7,5 V, Current input 150 mA, MCS diodes bias 2,5 V, having a Wavelength region 450 to 700 nm, Isoilluminance line 4×5500 cd and Sensor working distance 15 to 25 mm.

Using this optic sensor or another multi-channeled light detector, provides for a plurality of simultaneous and/or subsequentive different measurement procedures in one cell tube. Thus, according to one novel embodiment of the present invention, each analytical photochemical reaction known in the literature is suitable to be conducted. For the sake of an example, after chlorine determination, samples are taken for cyanides content, heavy metal content etc.

Reference is still made to FIGS. 1A and 1B, showing an opening (8n) perpendicular to the axle of opening (6) and (8). This optional opening is especially useful for light scattering measurements. It is acknowledged in this respect that more openings are possible and their location & size is primarily depended upon the measurement to be taken.

In order to seal the measurement volume provided by the measuring cell, the measuring tube and the shaker, a plurality of O-rings (12a-12d) are presented. According one embodiment of the present invention, at least portion of said 0-rings are located on the shaker (5).

As presented in FIGS. 1A and 1B, the shaker is having at least two portions: the portion located adjacent to the measuring tube (5in), and the portion located somewhat lower, at the lower portion of the measuring cell (5out). The outer diameter of the (5in) portion is smaller than the (5out) portion, providing a recess like configuration at the (5in) rim. Said recess is adapted to be in communication with the brush (not shown).

Reference is made now to FIG. 2A, presenting a cross section of one shaker, comprising a lower portion (5out), upper portion (5in) and the internal open bore, that provides a free fluid communication from inlet (2a) to outlet (2b). Brush fibers (14) are located at the (5in) portion of the shaker. FIG. 2B presents the same from a top view.

It is acknowledged in this respect that various shaker shapes can be used. Moreover, it is in the scope of the invention wherein various shaker shapes are designed for special reactions, fluid characteristics etc. Thus, various (5in) portions are to be used, and various brush arrangements are possible. Only for example only, a screw-like contour or either the (5in) and/or the brush fibers where found useful for various systems for determining pool's water and samples of running waters.

Lastly, it is another goal for the present invention to present a useful method for automatically mixing of fluids and/or reagents and for handsfree physical cleansing of the inner core of spectrophotometric measuring cells. Said method comprises of the following step: (a) filling the measurement cell with fluids; (b) striking the shaker at least one time, so the brush is physically cleansing the inner wall of the measuring tube; (c) calibrating for zero reading; (d) flashing the measurement cell with fresh fluids; (e) sealing the cell's outlets; (f) filing sampled fluids and/or reagents utilized for a photochemical reaction so a non-homogenized admixture is obtained; (g) striking the shaker a plurality of times so a homogenized solution is obtained and so bubbles of entrapped air or gas are purged from the cell; (h) measuring a predetermined spectrum of the solution; and (i) opening the cell's outlets and flashing the colored fluids out of the cell by means of fresh fluids.

The invention claimed is:

1. A spectrophotometric measuring cell comprising:
   a measuring cell having a free fluid passageway throughout its inner bore from an inlet to an outlet, said measuring cell comprising a light-transparent measuring tube having a longitudinal axis a and an inner bore of a diameter b,
   a shaker, accommodated in said inner bore of said measuring tube, said shaker being operative to strike back and forth along the longitudinal axis a, said shaker comprising a brush of an outer diameter b, said brush being adapted to provide an effective physical cleansing of the inner wall of the cell at the time the shaker is moving along the longitudinal axis; and
   an actuator, located outside said tube, adapted to actuate said shaker.

2. The measuring cell according to claim 1 and also comprising at least one of a monochromatic wavelength detector and a multi-channel RGB light emission detector.

3. The measuring cell according to claim 1, wherein the light-transparent measuring tube comprises at least one of a light transparent glass, quartz and a polymer.

4. The measuring cell according to claim 1, wherein at least a portion of the shaker is made of stainless steel.

5. The measuring cell according to claim 1, wherein the brush is made of nylon fibers.

6. The measuring cell according to claim 1, wherein the actuator is at least one electromagnetic coil, adapted to actuate the shaker magnetically.

7. The measuring cell according to claim 1, wherein said actuator comprises at least two electromagnetic actuators, at least one of said electromagnetic actuators being adapted to move the shaker in a first direction along said longitudinal axis, and at least one of said electromagnetic actuators being adapted to move the shaker in a second direction opposite said first direction.

8. The measuring cell according to claim 1 and wherein said fluid comprises water from at least one of a swimming pool, a water treatment facility, a sewage treatment plant, a drinking water system and a cooling tower.

9. The measuring cell according to claim 1 and also comprising means to measure at least one of pH, Redox, free chlorine content, light scattering, turbidity and temperature of a fluid located in said measuring tube.

10. A method for mixing at least one fluid and at least one reagent in a spectrophotometric measuring cell and for providing hands free cleaning of an inner core of the spectrophotometric measuring cell, the method comprising:
    providing a spectrophotometric measuring cell having a free fluid passageway throughout its inner bore from an inlet to an outlet, said measuring cell including a light-transparent measuring tube having a longitudinal axis a and an inner bore of a diameter b, a shaker, accommodated in said inner bore of said measuring tube, said shaker being operative to strike back and forth along the longitudinal axis, said shaker comprising a brush of an outer diameter b, and an actuator, located outside said tube, adapted to actuate said shaker;
    filling the measurement cell with fluid;
    actuating the shaker to strike back and forth at least once, said brush thereby cleaning the inner wall of the measuring tube;
    calibrating for zero reading;
    flushing the measurement cell;
    sealing the outlet;
    filling said cell with at least one fluid sample and at least one reagent, thereby obtaining a non-homogenized admixture; and
    actuating the shaker to strike back and forth a plurality of times, thereby obtaining a homogenized solution.

11. A method according to claim 10 and wherein said actuating also comprises purging entrapped gas from said cell.

12. A method according to claim 10 and also comprising measuring a predetermined spectrum of said homogenized solution.

13. A method of cleaning an inner bore of a measuring tube of a spectrophotometric measuring cell, comprising:
    providing a spectrophotmetric measuring cell including a measuring cell having a free fluid passageway throughout its inner bore from an inlet to an outlet, said measuring cell comprising a light-transparent measuring tube having a longitudinal axis and an inner bore and a shaker, accommodated in said inner bore of said measuring tube, said shaker including a brush;
    filling the measurement cell with fluid; and
    actuating said shaker, including said brush, to strike back and forth at least once along said longitudinal axis, said brush thereby cleaning said inner bore of said measuring tube.

* * * * *